United States Patent
Ford et al.

(10) Patent No.: US 11,536,726 B2
(45) Date of Patent: Dec. 27, 2022

(54) MASS SPECTROMETRY ASSAY METHOD FOR DETECTION AND QUANTITATION OF LIVER FUNCTION METABOLITES

(71) Applicant: Metabolon, Inc., Morrisville, NC (US)

(72) Inventors: Lisa Ford, Durham, NC (US); Kirk L. Pappan, Rougemont, NC (US); Tiffany A. Freed, Apex, NC (US); Kelsey M. Eason, Durham, NC (US)

(73) Assignee: Metabolon, Inc., Morrisville, NC (US)

( * ) Notice: Subject to any disclaimer, the term of this patent is extended or adjusted under 35 U.S.C. 154(b) by 175 days.

(21) Appl. No.: 17/043,165

(22) PCT Filed: Apr. 1, 2019

(86) PCT No.: PCT/US2019/025109
§ 371 (c)(1),
(2) Date: Sep. 29, 2020

(87) PCT Pub. No.: WO2019/195128
PCT Pub. Date: Oct. 10, 2019

(65) Prior Publication Data
US 2021/0148924 A1  May 20, 2021

Related U.S. Application Data

(60) Provisional application No. 62/652,346, filed on Apr. 4, 2018.

(51) Int. Cl.
| | |
|---|---|
| *G01N 33/68* | (2006.01) |
| *G01N 30/72* | (2006.01) |
| *G01N 33/49* | (2006.01) |
| *H01J 49/00* | (2006.01) |
| *H01J 49/04* | (2006.01) |
| *G01N 33/483* | (2006.01) |
| *G01N 33/52* | (2006.01) |
| *G01N 30/02* | (2006.01) |
| *G01N 30/04* | (2006.01) |

(52) U.S. Cl.
CPC ..... *G01N 33/6848* (2013.01); *G01N 30/7233* (2013.01); *G01N 33/483* (2013.01); *G01N 33/492* (2013.01); *G01N 33/52* (2013.01); *H01J 49/0009* (2013.01); *H01J 49/0095* (2013.01); *H01J 49/0431* (2013.01); *G01N 2030/027* (2013.01); *G01N 2030/045* (2013.01)

(58) Field of Classification Search
CPC ............ G01N 33/6848; G01N 33/492; G01N 33/6842; G01N 33/92; G01N 33/94; G01N 33/9406; G01N 33/483; G01N 33/52; G01N 30/7233; G01N 2030/027; G01N 2030/045; G01N 2570/00; G01N 2800/085; H01J 49/0009; H01J 49/0095; H01J 49/0431

USPC .......................................................... 250/282
See application file for complete search history.

(56) References Cited

U.S. PATENT DOCUMENTS

| | | | |
|---|---|---|---|
| 2006/0014294 A1 | 1/2006 | Contreras et al. | |
| 2010/0148055 A1* | 6/2010 | Caulfield | H01J 49/00 250/282 |
| 2010/0155595 A1* | 6/2010 | Ghoshal | H01J 49/0031 250/283 |
| 2015/0355197 A1 | 12/2015 | Kamp et al. | |
| 2020/0166519 A1* | 5/2020 | Ford | G01N 33/6848 |

FOREIGN PATENT DOCUMENTS

| | | |
|---|---|---|
| WO | 2014200816 A1 | 12/2014 |
| WO | 2016081534 A1 | 5/2016 |
| WO | 2017210097 A1 | 12/2017 |

OTHER PUBLICATIONS

WIPO; International Preliminary Report on Patentability for International Patent Application No. PCT/US19/25109 dated Oct. 15, 2020, 8 pages.
EPO; Extended European Search Report for European Patent Application No. 19782142.4 dated Dec. 9, 2021, 11 pages.
EPO; Communication pursuant to Rules 70(2) and 70a(2) EPC for European Patent Application No. 19782142.4 dated Jan. 5, 2022, 1 page.
Bell, Lauren N., et al., "Serum Metaboloic Signatures of Primary Biliary Cinhosis and Primary Sclersogin Cholangitis", Liver Int., vol. 35, No. 1, Jan. 2015, 25 pages.
ISA/US; International Search Report and Written Opinion for International Patent Application No. PCT/US19/25109 dated Jul. 26, 2019, 11 pages.

* cited by examiner

*Primary Examiner* — Kiet T Nguyen
(74) *Attorney, Agent, or Firm* — NK Patent Law

(57) ABSTRACT

A method for determining in a sample, by mass spectrometry, the amount of one or more analytes selected from the group consisting of 12,13-DiHOME, 3-hydroxybutyrate (BHBA), 3-hydroxyoctanoate, 3-methylglutarylcarnitine, 3-ureidopropionate, 7-alpha-hydroxy-4-cholesten-3-one (7-Hoca), citrate, fucose, fumarate, gamma-tocopherol, glutamate, glutarate, glycerol, glycochenodeoxycholate, glycocholate, hypoxanthine, maleate, malonate, mannose, orotate, 2,3-pyrdinedicarboxylate, ribose, serine, taurine, taurochenodeoxycholate, taurocholate, palmitoleate, linolenate, xanthine, xylitol, and combinations thereof is described. The method comprises subjecting the sample to an ionization source under conditions suitable to produce one or more ions detectable by mass spectrometry from each of the one or more analytes; measuring, by mass spectrometry, the amount of the one or more ions from each of the one or more analytes; and using the measured amount to determine the amount of each of the one or more analytes in the sample.

13 Claims, No Drawings

MASS SPECTROMETRY ASSAY METHOD FOR DETECTION AND QUANTITATION OF LIVER FUNCTION METABOLITES

CROSS-REFERENCE TO RELATED APPLICATIONS

This application is a U.S. National Stage application of International Patent Application No. PCT/US2019/025109, filed on Apr. 1, 2019, which claims the benefit of U.S. Provisional Application No. 62/652,346, filed on Apr. 4, 2018, the entire contents of which are incorporated by reference herein.

BACKGROUND

The following information to describe the background of the invention is provided to assist the understanding of the invention and is not admitted to constitute or describe prior art to the invention.

Liver function may be affected by various lifestyles, diseases, and disorders including, for example, diet, alcohol abuse, fatty liver disease, infections, medications, and cancer. Often, a significant amount of liver tissue may be damaged before a person experiences symptoms of liver dysfunction. Currently, the most common tests to assess liver function include measurements of specific enzymes and proteins in blood. These tests include alanine aminotransferase (ALT), aspartate aminotransferase (AST), alkaline phosphatase (ALP), gamma-glutamyl transferase (GGT), and serum cholinesterase (ChE) total cholesterol, total triglycerides, albumin, albumin/globulin ratio, total protein, direct bilirubin, and total bilirubin.

Current liver blood tests may provide a first indication of liver disease including Nonalcoholic Fatty Liver Disease (NAFLD), nonalcoholic steatohepatitis (NASH), fibrosis, and cirrhosis, but the tests do not detect early changes in liver function and are not able to distinguish between the diseases. When further evaluation shows no apparent reason for liver disease (such as medications, viral hepatitis, or excessive use of alcohol) and when x-rays or imaging studies of the liver show fat, NASH is suspected, but the only means of proving a diagnosis of NASH and separating it from simple fatty liver is a liver biopsy. A liver biopsy is also required to determine the presence and staging of liver fibrosis. Currently, no blood tests or scans can reliably provide this information. A liver biopsy which is an invasive procedure that requires a needle to be inserted through the skin and the removal of a small piece of the liver. The procedure is painful and associated with risk of excessive bleeding. Therefore, there exists a need for a less invasive method (i.e. a method that would not require a liver biopsy) to assess the function of the liver that supplements currently available clinical assays.

The prevalence of NAFLD, which encompasses an entire histologic spectrum ranging from simple, benign hepatic steatosis to NASH characterized by lipid accumulation, inflammation, hepatocyte ballooning, and varying degrees of fibrosis, continues to increase in concert with the obesity epidemic. Despite increasing awareness of obesity-related liver disease, the pathogenesis of NAFLD and NASH is poorly understood, and there are no FDA-approved therapies with NASH as an indication. Diagnosis of NASH remains complicated and with significant risk due to the requirement for an invasive liver biopsy. Therefore, identification of a profile of blood-based metabolite biomarkers useful to assess liver function including the ability to diagnose and stage NAFLD is a significant unmet medical need.

Described herein are methods for the detection and quantitation of analytes useful for the assessment of liver function in a biological sample. The measured analytes may include a panel comprised of one or more analytes selected from 12,13-DiHOME, 3-hydroxybutyrate (BHBA, 3-HB), 3-hydroxyoctanoate (3-hydroxyoctanoic acid), 3-methylglutarylcarnitine, 3-ureidopropionate (3-ureidopropionic acid), 7-alpha-hydroxy-4-cholesten-3-one (7-Hoca), citrate (citric acid), fucose, fumarate (fumaric acid), gamma-tocopherol, glutamate (glutamic acid), glutarate (glutaric acid), glycerol, glycochenodeoxycholate (glycochenodeoxycholic acid), glycocholate (glycocholic acid), hypoxanthine, maleate (maleic acid), malonate (malonic acid), mannose, orotate (orotic acid), 2,3-pyrdinedicarboxylate, ribose, serine, taurine, taurochenodeoxycholate (taurochenodeoxycholic acid), taurocholate (taurocholic acid), palmitoleate (palmitoleic acid), linolenate (linolenic acid), xanthine, xylitol. Combinations of these analytes may be used along with traditional clinical biochemistry assays including total cholesterol, total triglycerides, albumin, albumin/globulin ratio, total protein, direct bilirubin, total bilirubin, alanine aminotransferase (ALT), aspartate aminotransferase (AST), alkaline phosphatase (ALP), gamma-glutamyl transferase (GGT), and serum cholinesterase (ChE). The results of these methods allow assessment of liver function including the assessment of the presence, absence or level (stage) of inflammation, injury, oxidative stress, fibrosis, steatosis, and NASH. Advantages of this approach include its non-invasive nature and ease of use in routine clinical practice for assessment of liver function. Further, the metabolite assays require a small sample size, do not require derivatization and can be performed using mass spectrometry analysis methods.

SUMMARY

In a first aspect of the invention, a method comprises detecting and determining the amount of a panel of analytes comprised of one or more analytes selected from the group consisting of 12,13-DiHOME, 3-hydroxybutyrate (BHBA), 3-hydroxyoctanoate, 3-methylglutarylcarnitine, 3-ureidopropionate, 7-alpha-hydroxy-4-cholesten-3-one (7-Hoca), citrate, fucose, fumarate, gamma-tocopherol, glutamate, glutarate, glycerol, glycochenodeoxycholate, glycocholate, hypoxanthine, maleate, malonate, mannose, orotate, 2,3-pyrdinedicarboxylate, ribose, serine, taurine, taurochenodeoxycholate, taurocholate, palmitoleate, linolenate, xanthine, xylitol, and combinations thereof in a sample by mass spectrometry. In one embodiment, the method comprises subjecting the sample to an ionization source under conditions suitable to produce one or more ions detectable by mass spectrometry from each of the one or more analytes. In another embodiment, the analytes are not derivatized prior to ionization. Methods to extract the analytes from biological samples and to chromatographically separate the analytes prior to detection by mass spectrometry are also provided.

In an embodiment, the mass spectrometry is tandem mass spectrometry.

In an embodiment, the method includes determining the amount of a plurality of analytes, such as, for example, the amount of one or more analytes selected from the group consisting of 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, and Linolenic acid in a sample by mass spectrometry using a single injection.

In an embodiment, the method includes determining the amount of a plurality of analytes, such as, for example, the amount of one or more analytes selected from the group consisting of 12,13-DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, and Taurocholate in a sample by mass spectrometry using a single injection.

In an embodiment, the method includes determining the amount of a plurality of analytes, such as, for example, the amount of one or more analytes selected from the group consisting of 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, and Xylitol in a sample by mass spectrometry using a single injection.

In some embodiments, the amounts of two or more, three or more, four or more, five or more, six or more, or seven or more of the analytes are determined. When the amounts of two or more analytes are determined, the two or more analytes may be referred to as a "plurality of analytes". Where a plurality of analytes is quantified, the analytes may be referred to as a "panel" or a "panel of analytes".

In one embodiment, the run time may be 9 minutes or less. In another embodiment, the run time may be less than 8 minutes.

In embodiments, the sample may be a plasma sample or a serum sample.

The sample volume may be 10 µl to 200 µl. For example, the sample volume may be 10 µl, 15, 20, 25, 30, 40, 50 µl, 60, 70, 80, 90, 100, 120, 140, 160, 180 or 200 µl or any other volume between 10 and 200 µl.

DETAILED DESCRIPTION

Methods are described for measuring the amount of one or more analytes selected from the group of metabolites consisting of: 12,13-DiHOME, 3-hydroxybutyrate (BHBA), 3-hydroxyoctanoate, 3-methylglutarylcarnitine, 3-ureidopropionate, 7-alpha-hydroxy-4-cholesten-3-one (7-Hoca), citrate, fucose, fumarate, gamma-tocopherol, glutamate, glutarate, glycerol, glycochenodeoxycholate, glycocholate, hypoxanthine, maleate, malonate, mannose, orotate, 2,3-pyrdinedicarboxylate, ribose, serine, taurine, taurochenodeoxycholate, taurocholate, palmitoleate, linolenate, xanthine, xylitol, and combinations thereof, in a sample. Mass spectrometric methods are described for quantifying single and multiple analytes in a sample using a single injection method. The methods may use a liquid chromatography step such as UPLC or HILIC to perform a separation (purification, enrichment) of selected analytes combined with methods of mass spectrometry, thereby providing a high-throughput assay system that is amenable to automation for quantifying a plurality of analytes in a sample.

The methods presented herein provide advantages over current methods to measure these analytes. The ability to quantifiably measure, in a single injection, a plurality of analytes in various combinations, reduces the time required to obtain analysis results, uses fewer resources in terms of laboratory disposables (e.g., tubes, pipette tips, reagents), laboratory instruments and human resources. These improvements lead to savings by decreasing the costs of the assays and increasing the instrument and laboratory capacity for sample analysis.

Prior to describing this invention in further detail, the following terms are defined.

Definitions

The term "solid phase extraction" refers to a sample preparation process where components of complex mixture (i.e., mobile phase) are separated according to their physical and chemical properties using solid particle chromatographic packing material (i.e. solid phase or stationary phase). The solid particle packing material may be contained in a cartridge type device (e.g. a column).

The term "separation" refers to the process of separating a complex mixture into its component molecules or metabolites. Common, exemplary laboratory separation techniques include electrophoresis and chromatography.

The term "chromatography" refers to a physical method of separation in which the components (i.e., chemical constituents) to be separated are distributed between two phases, one of which is stationary (stationary phase) while the other (the mobile phase) moves in a definite direction. The mobile phase may be gas ("gas chromatography", "GC") or liquid ("liquid chromatography", "LC"). Chromatographic output data may be used in embodiments of the method described herein.

The term "liquid chromatography" or "LC" refers to a process of selective inhibition of one or more components of a fluid solution as the fluid uniformly moves through a column of a finely divided substance or through capillary passageways. The inhibition results from the distribution of the components of the mixture between one or more stationary phases and the mobile phase(s) as the mobile phase(s) move relative to the stationary phase(s). Examples of "liquid chromatography" include "Reverse phase liquid chromatography" or "RPLC", "high performance liquid chromatography" or "HPLC", "ultra-high performance liquid chromatography" or "UPLC" or "UHPLC", or hydrophilic interaction chromatography or "HILIC".

The term "retention time" refers to the elapsed time in a chromatography process since the introduction of the sample into the separation device. The retention time of a constituent of a sample refers to the elapsed time in a chromatography process between the time of injection of the sample into the separation device and the time that the constituent of the sample elutes (e.g., exits from) the portion of the separation device that contains the stationary phase.

The term "retention index" of a sample component refers to a number, obtained by interpolation (usually logarithmic), relating the retention time or the retention factor of the sample component to the retention times of standards eluted before and after the peak of the sample component, a mechanism that uses the separation characteristics of known standards to remove systematic error.

The term "separation index" refers to a metric associated with chemical constituents separated by a separation technique. For chromatographic separation techniques, the separation index may be retention time or retention index. For non-chromatographic separation techniques, the separation index may be physical distance traveled by the chemical constituent.

As used herein, the terms "separation information" and "separation data" refer to data that indicates the presence or absence of chemical constituents with respect to the separation index. For example, separation data may indicate the presence of a chemical constituent having a particular mass eluting at a particular time. The separation data may indicate that the amount of the chemical constituent eluting over time rises, peaks, and then falls. A graph of the presence of the chemical constituent plotted over the separation index (e.g., time) may display a graphical peak. Thus, within the context of separation data, the terms "peak information" and "peak data" are synonymous with the terms "separation information" and "separation data".

The term "Mass Spectrometry" (MS) refers to a technique for measuring and analyzing molecules that involves ionizing or ionizing and fragmenting a target molecule, then analyzing the ions, based on their mass/charge ratios, to produce a mass spectrum that serves as a "molecular fingerprint". Determining the mass/charge ratio of an object may be done through means of determining the wavelengths at which electromagnetic energy is absorbed by that object. There are several commonly used methods to determine the mass to charge ratio of an ion, some measuring the interaction of the ion trajectory with electromagnetic waves, others measuring the time an ion takes to travel a given distance, or a combination of both. The data from these fragment mass measurements can be searched against databases to obtain identifications of target molecules.

The terms "operating in negative mode" or "operating in negative multiple reaction monitoring (MRM) mode" or "operating in negative ionization mode" refer to those mass spectrometry methods where negative ions are generated and detected. The terms "operating in positive mode" or "operating in positive multiple reaction monitoring (MRM) mode" or "operating in positive ionization mode" refer to those mass spectrometry methods where positive ions are generated and detected.

The term "mass analyzer" refers to a device in a mass spectrometer that separates a mixture of ions by their mass-to-charge ("m/z") ratios.

The term "m/z" refers to the dimensionless quantity formed by dividing the mass number of an ion by its charge number. It has long been called the "mass-to-charge" ratio.

As used herein, the term "source" or "ionization source" refers to a device in a mass spectrometer that ionizes a sample to be analyzed. Examples of ionization sources include electrospray ionization (ESI), atmospheric pressure chemical ionization (APCI), heated electrospray ionization (HESI), atmospheric pressure photoionization (APPI), flame ionization detector (FID), matrix-assisted laser desorption ionization (MALDI), etc.

As used herein, the term "detector" refers to a device in a mass spectrometer that detects ions.

The term "ion" refers to any object containing a charge, which can be formed for example by adding electrons to or removing electrons from the object.

The term "mass spectrum" refers to a plot of data produced by a mass spectrometer, typically containing m/z values on x-axis and intensity values on y-axis.

The term "scan" refers to a mass spectrum that is associated with a particular separation index. For example, systems that use a chromatographic separation technique may generate multiple scans, each scan at a different retention time.

The term "run time", refers to the time from sample injection to generation of the instrument data.

The term "tandem MS" refers to an operation in which a first MS step, called the "primary MS", is performed, followed by performance of one or more of a subsequent MS step, generically referred to as "secondary MS". In the primary MS, an ion, representing one (and possibly more than one) chemical constituent, is detected and recorded during the creation of the primary mass spectrum. The substance represented by the ion is subjected to a secondary MS, in which the substance of interest undergoes fragmentation in order to cause the substance to break into subcomponents, which are detected and recorded as a secondary mass spectrum. In a true tandem MS, there is an unambiguous relationship between the ion of interest in the primary MS and the resulting peaks created during the secondary MS. The ion of interest in the primary MS corresponds to a "parent" or precursor ion, while the ions created during the secondary MS correspond to sub-components of the parent ion and are herein referred to as "daughter" or "product" ions.

Thus, tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion. Tandem MS may be repeated on daughter ions to determine "grand-daughter" ions, for example. Thus, tandem MS is not limited to two-levels of fragmentation, but is used generically to refer to multi-level MS, also referred to as "MS$^n$". The term "MS/MS" is a synonym for "MS$^2$". For simplicity, the term "daughter ion" hereinafter refers to any ion created by a secondary or higher-order (i.e., not the primary) MS.

The "level" of one or more biomarkers means the absolute or relative amount or concentration of the biomarker measured in the sample.

"Analyte" or, "metabolite" as used herein refers to 12,13-DiHOME, 3-hydroxybutyrate (BHBA), 3-hydroxyoctanoate, 3-methylglutarylcarnitine, 3-ureidopropionate, 7-alpha-hydroxy-4-cholesten-3-one (7-Hoca), citrate, fucose, fumarate, gamma-tocopherol, glutamate, glutarate, glycerol, glycochenodeoxycholate, glycocholate, hypoxanthine, maleate, malonate, mannose, orotate, 2,3-pyrdinedicarboxylate, ribose, serine, taurine, taurochenodeoxycholate, taurocholate, palmitoleate, linolenate, xanthine, xylitol, and combinations thereof. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000).

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological fluid or tissue such as, for example, blood, blood plasma (plasma), blood serum (serum), urine, cerebral spinal fluid (CSF), feces, or tissue.

"Subject" means any animal, but is preferably a mammal, such as, for example, a human, monkey, mouse, dog, rabbit or rat.

I. Sample Preparation and Quality Control (QC)

Sample extracts containing analytes are prepared by isolating the analytes away from the macromolecules (e.g., proteins, nucleic acids, lipids) that may be present in the sample. Some or all analytes in a sample may be bound to proteins. Various methods may be used to disrupt the interaction between analyte(s) and protein prior to MS analysis. For example, the analytes may be extracted from a sample to produce a liquid extract, while the proteins that may be present are precipitated and removed. Proteins may be precipitated using, for example, a solution of ethyl acetate or methanol. To precipitate the proteins in the sample, an ethyl acetate or methanol solution is added to the sample, then the mixture may be spun in a centrifuge to separate the liquid supernatant, which contains the extracted analytes, from the precipitated proteins In other embodiments, analytes may be released from protein without precipitating the protein. For example, a formic acid solution may be added to the sample to disrupt the interaction between protein and analyte. Alternatively, ammonium sulfate, a solution of formic acid in ethanol, or a solution of formic acid in methanol may be added to the sample to disrupt ionic interactions between protein and analyte without precipitating the protein. In one example, a solution of acetonitrile, methanol, water, and formic acid may be used to extract analytes from the sample.

In some embodiments the extract may be subjected to various methods including liquid chromatography, electrophoresis, filtration, centrifugation, and affinity separation as described herein to purify or enrich the amount of the selected analyte relative to one or more other components in the sample.

To assess, for example, precision, accuracy, calibration range, or analytical sensitivity of methods of detecting and quantifying analytes, quality control (QC) samples may be used. The concentration of a given analyte(s) to be used in a QC sample may be determined based on lower limit of quantitation (LLOQ) or upper limit of quantitation (ULOQ) of the given analyte(s), as detected in a sample. In one example, the LLOQ may be represented by the concentration of a standard (e.g., Standard A), and the ULOQ may be represented by the concentration of a second standard (e.g., Standard H). The Low QC value may be set at a concentration of about 3×LLOQ, the Mid QC value may be at a concentration of about 25-50% of High QC, and the High QC value may be at a concentration of about 80% of the ULOQ. The QC target concentration levels may be chosen based on a combination of the Analytical Measurement Range (AMR) and the frequency of sample results as measured in a set of representative samples.

II. Chromatography

Prior to mass spectrometry, the analyte extract may be subjected to one or more separation methods such as electrophoresis, filtration, centrifugation, affinity separation, or chromatography. In one embodiment the separation method may comprise liquid chromatography (LC), including, for example, ultra high performance LC (UHPLC).

In some embodiments, UHPLC may be conducted using a reversed phase column chromatographic system, hydrophilic interaction chromatography (HILIC), or a mixed phase column chromatographic system.

The column heater (or column manager) for LC may be set at a temperature of from about 25° C. to about 80° C. For example, the column heater may be set at about 30° C., 40° C., 50° C., 60° C., 70° C., etc.

In an example, UHPLC may be conducted using HILIC system. In another example, UHPLC may be conducted using a reversed phase column chromatographic system. The system may comprise two or more mobile phases. Mobile phases may be referred to as, for example, mobile phase A, mobile phase B, mobile phase A', and mobile phase B'.

In an exemplary embodiment using two mobile phases, A and B, mobile phase A may comprise ammonium bicarbonate in water, and mobile phase B may comprise ammonium bicarbonate in methanol and water. The concentration of ammonium bicarbonate may range from 1 mM to 10 mM, and the concentration of methanol may range from 1% to 99%. In some examples, the concentration of ammonium bicarbonate in mobile phase A may be 3.0, 3.5, 4.0, 4.5, 5.0, 5.5, 6.0, 6.5, 7.0, 7.5, 8.0, or 8.5 mM. In some examples, the concentration of ammonium bicarbonate in mobile phase B may be 3.0, 3.5, 4.0, 4.5, 5.0, 5.5, 6.0, 6.5, 7.0, 7.5, 8.0, or 8.5 mM, and the concentration of methanol may be 90, 91, 92, 93, 94, 95, 96, 97, 98, or 99%.

In one example, linear gradient elution may be used for chromatography. The starting conditions for linear gradient elution may include the concentration of a mobile phase (e.g., mobile phase B) and/or the flow rate of a mobile phase through the column (e.g., mobile phase B). The starting conditions may be optimized for the separation and/or retention of one or more analytes. The gradient conditions may also be optimized for the separation and/or retention of analytes and may vary depending on the flow rate selected. For example, initial conditions may be 0.5% mobile phase B and 350 µL/min flow rate. Mobile phase B may be increased to 50-75%, increased to about 75-99% at about 4 minutes, maintained for 1-2 min. Mobile phase B may revert to 0.5% at 6.2 min where it may be maintained for 1-2 min. for equilibration for the next sample injection. The total run time may be 7.5 minutes or less.

In another example, mobile phase A may comprise perfluoropentanoic acid (PFPA), formic acid, and water, and mobile phase B may comprise PFPA, formic acid, and methanol. The concentration of PFPA may be from about 0.01 to about 0.500%, and the concentration of formic acid may be from about 0.001 to about 1.0%. In some examples, the concentration of perfluoropentanoic acid (PFPA) in mobile phase A may be 0.03, 0.04, 0.05, 0.06, 0.07, 0.08, 0.09, 0.1, 0.2, or 0.3%, and the concentration of formic acid may be 0.001, 0.005, 0.1, 0.2, 0.3, 0.4, or 0.5%. In other examples, the concentration of PFPA in mobile phase B may be 0.03, 0.04, 0.05, 0.06, 0.07, 0.08, 0.09, 0.1, 0.2, or 0.3%, and the concentration of formic acid may be 0.001, 0.005, 0.1, 0.2, 0.3, 0.4, or 0.5%. Linear gradient elution may be used for chromatography. For example, initial conditions may be 5% mobile phase B and 450 µL/min flow rate. Mobile phase B may be increased to about 75-99% at about 5 minutes, and maintained for about 3 min. Mobile phase B may revert to 5% at 8 min where it may be maintained for about one minute for equilibration for the next sample injection. The total run time may be 9 minutes or less.

In yet other embodiments, mobile phase A may comprise ammonium formate, acetonitrile, methanol, and water, and mobile phase B may comprise ammonium formate and acetonitrile. The concentration of ammonium formate in mobile phase A may range from 0.1 mM to 100 mM, and the concentration of acetonitrile may range from 0% to 100%. In some examples, the concentration of ammonium formate in mobile phase A may be 1 mM, 5 mM, 10 mM, 15 mM, 20 mM, 25 mM, or 50 mM, and the concentration of acetonitrile may be 60, 70, 80, or 90%. In other examples, the concentration of ammonium formate in mobile phase B may be 1 mM, 5 mM, 10 mM, 15 mM, 20 mM, 25 mM, or 50 mM, and the concentration of acetonitrile may be 30%, 40%, 50%, or 60%. Linear gradient elution may be used for chromatography. For example, initial conditions may be 5% mobile phase B and 500 µL/min flow rate. Mobile phase B may be increased to about 40-60% at about 3-4 minutes, increased to about 75-99% at 4-6 minutes, and maintained for about 1 min. Mobile phase B may revert to 5% at 6-7 min where it may be maintained for about one minute for equilibration for the next sample injection. The total run time may be 7.5 minutes or less.

III. Mass Spectrometry and Quantitation

One or more analytes may be ionized by, for example, mass spectrometry. Mass spectrometry is performed using a mass spectrometer that includes an ionization source for ionizing the fractionated sample and creating charged molecules for further analysis. Ionization of the sample may be performed by, for example, electrospray ionization (ESI). Other ion sources may include, for example, atmospheric pressure chemical ionization (APCI), heated electrospray ionization (HESI), atmospheric pressure photoionization (APPI), flame ionization detector (FID), or matrix-assisted laser desorption ionization (MALDI). The choice of ionization method may be determined based on a number of considerations. Exemplary considerations include the analyte to be measured, type of sample, type of detector, and the choice of positive or negative mode. In some examples, mass spectrometry methods may be divided into two or more periods to increase sensitivity.

The one or more analytes may be ionized in positive or negative mode to create one or more ions. For example, the analytes 12,13-DiHOME, 3-methylglutarylcarnitine, 7-alpha-hydroxy-4-cholesten-3-one (7-Hoca), gamma-tocopherol, glutamate, glycochenodeoxycholate, glycocholate, hypoxanthine, serine, and taurocholate, may be ionized in positive mode. In yet another example, the analytes 12,13-DiHOME, 3-hydroxybutyrate (BHBA), 3-hydroxyoctanoate, 3-ureidopropionate, citrate, fucose, fumarate, glutamate, glutarate, glycerol, glycochenodeoxycholate, glycocholate, hypoxanthine, maleate, malonate, mannose, orotate, 2,3-pyridinedicarboxylate, ribose, serine, taurine, taurochenodeoxycholate, taurocholate, palmitoleate, linolenate, xanthine, xylitol may be ionized in negative mode. In some examples, analytes may be ionized in positive mode and negative mode in a single injection.

In one example, the analytes 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, and Linolenic acid may be ionized in negative mode and may be measured in a single injection. In another example, the analytes 12,13-DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, and Taurocholate may be ionized in positive mode and may be measured in a single injection. In yet another example, the analytes 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, and Xylitol may be ionized in negative mode and may be measured in a single injection.

Mass spectrometer instrument settings may be optimized for the given analysis method and/or for the particular mass spectrometer used. The instrument may use various gases, for example, nitrogen, helium, argon, or zero air. In an embodiment, mass spectrometry may be performed using AB Sciex QTrap 5500 mass spectrometers. In one example, the mass spectrometer may be operated in positive multiple reaction monitoring (MRM) mode. The ionspray voltage setting may range from about 0.5 kV to about 6.0 kV; in one embodiment the voltage may be set at 5.5 kV. The source temperature may range from about 350° C. to about 600° C.; in one embodiment the source temperature may be set at 500° C. The curtain gas may range from about 10 to about 55 psi; in one embodiment the curtain gas is set at 30 psi. The nebulizer and desolvation gas flow rates may range from about 0 to about 90 psi. In one embodiment the flow rates may be set at 70. The CAD gas setting may range from high to low; in one embodiment the collisionally activated dissociation (CAD) gas is set at medium. Declustering potential may range from about 20V to about 190V. The collision energy (CE) may range from about 10 V to about 70 V. The entrance potential (EP) may be about 10V. The collision cell exit potential (CXP) setting may range from about 2V to about 30V.

In another example, the MS instrument may be operated in negative MRM mode. Ionspray voltage settings may range from −0.5 kV to −5.5 kV; in one embodiment the voltage may be set at −4.5 kV. The source temperature may range from about 350° C. to 600° C.; in one embodiment the source temperature may be set at 500° C. The curtain gas may range from 10 to 40; in an embodiment the curtain gas may be set at 30. The nebulizer and desolvation gas flow rates may range from 40 to 90. In one embodiment the flow rates may be set at 70; in another embodiment, the flow rates may be set at 80. In another example the nebulizer gas flow rate may be set at 80 and the desolvation gas flow rate may be set at 65. The CAD gas may range from low to high. In one example the CAD may be set, for example, at medium. In another example, the CAD may be set at high. Declustering potential may range from about −10V to about −290V. The collision energy (CE) may range from about −10 V to about −130 V. The entrance potential (EP) may be about −10V. The collision cell exit potential (CXP) setting may range from about −5V to about −35V.

After a sample has been ionized, the positively or negatively charged ions may be analyzed to determine a mass-to-charge ratio. Exemplary suitable analyzers for determining mass-to-charge ratios include quadrupole analyzers, ion trap analyzers, and time of flight analyzers. The ions may be detected using, for example, a selective mode or a scanning mode. Exemplary scanning modes include MRM and selected reaction monitoring (SRM).

Analysis results may include data produced by tandem MS. In exemplary embodiments, tandem MS may be accurate-mass tandem MS. For example, the accurate-mass tandem mass spectrometry may use a quadrupole time-of-flight (Q-TOF) analyzer. Tandem MS allows the creation of data structures that represent the parent-daughter relationship of chemical constituents in a complex mixture. This relationship may be represented by a tree-like structure illustrating the relationship of the parent and daughter ions to each other, where the daughter ions represent sub-components of the parent ion.

For example, a primary mass spectrum may contain five distinct ions, which may be represented as five graphical peaks. Each ion in the primary MS may be a parent ion. Each parent ion may be subjected to a secondary MS that produces a mass spectrum showing the daughter ions for that particular parent ion.

The parent/daughter relationship may be extended to describe the relationship between separated components (e.g., components eluting from the chromatography state) and ions detected in the primary MS, and to the relationship between the sample to be analyzed and the separated components.

The mass spectrometer typically provides the user with an ion scan (i.e., a relative abundance of each ion with a particular mass/charge over a given range). Mass spectrometry data may be related to the amount of the analyte in the original sample by a number of methods. In one example, a calibration standard is used to generate a standard curve (calibration curve) so that the relative abundance of a given ion may be converted into an absolute amount of the original analyte. In another example, the calibration standard may be an external standard and a standard curve may be generated based on ions generated from those standards to calculate the quantity of one more analytes. In a further example, the external standard may be an unlabeled analyte.

Internal standards may be added to calibration standards and/or test samples. An internal standard may be used to account for loss of analytes during sample processing in order to get a more accurate value of a measured analyte in the sample. The ratio of analyte peak area to internal standard peak area in the levels of the calibration standards may be used to generate a calibration curve and quantitate samples. One or more isotopically labeled analogs of analytes, for example, 12,13-DiHOME-d4, 13C2-Glutarate, 13C415N2-Ureidopropionic acid, 3-Hydroxyoctanoic acid-d12, 7a-Hydroxy-4-cholesten-3-one-d7, Citric Acid-2,2,4,4-d4 acid, d4-3-hydroxybutyrate, D-Ribose-13C5, Fucose-13C6, Fumaric acid-13C4, Gamma-Tocopherol-d4, Glycerol 13C3, Glycochenodeoxycholic-d4 acid, Glycocholic-d4 acid, Hypoxanthine-13C5,15N4, L-Glutamic acid-d5, L-Serine (2,3,3-d3), Maleic acid 2,3-d2, Malonic Acid-d4, Mannose 13C6, Palmitoleic Acid-d14, Quinolinic acid 13C315N, Taurine-1,1,2,2-d4, Taurochenodeoxycholate-d4, Taurocholate-d4, Xylitol-d7, d4-linolenic acid, xanthine-13C15N2, orotate-13C15N2, and 3-methyl-glutaroylN-(methyl-d3)-carnitine may be used as internal standards.

The analysis data from the MS instrument may be sent to a computer and processed using computer software. In one example, peak area ratios of analyte to internal standard are fitted against the concentrations of the calibration standards using a statistical regression method for quantitation. In another example, the statistical regression is weighted linear least squares regression. The slope and intercept calculated using the calibration curve may be used to calculate the unknown concentrations of analytes in experimental samples.

After obtaining the concentration of the one or more liver panel analytes, the concentration values may be entered into a multivariate algorithm to generate a Liver Function Score. For example, the concentrations of two analytes, three analytes, four analytes, five analytes, or six or more analytes selected from the group consisting of 12,13-DiHOME, 3-hydroxybutyrate (BHBA), 3-hydroxyoctanoate, 3-methylglutarylcarnitine, 3-ureidopropionate, 7-alpha-hydroxy-4-cholesten-3-one (7-Hoca), citrate, fucose, fumarate, gamma-tocopherol, glutamate, glutarate, glycerol, glycochenodeoxycholate, glycocholate, hypoxanthine, maleate, malonate, mannose, orotate, 2,3-pyrdinedicarboxylate, ribose, serine, taurine, taurochenodeoxycholate, taurocholate, palmitoleate, linolenate, xanthine, and xylitol may be determined. In one example, one or more traditional clinical biochemistry assays including total cholesterol, total triglycerides, albumin, albumin/globulin ratio, total protein, direct bilirubin, total bilirubin, alanine aminotransferase (ALT), aspartate aminotransferase (AST), alkaline phosphatase (ALP), gamma-glutamyl transferase (GGT), and serum cholinesterase (ChE), may be used in combination with the concentration values of analytes obtained using the methods described herein. Traditional clinical biochemistry assays may be conducted using methods known in the art including, for example, using the ARCHITECT analyzer from Abbott.

IV. Kit

A kit for assaying one or more or a plurality of the liver panel analytes selected from the group consisting of 12,13-DiHOME, 3-hydroxybutyrate (BHBA), 3-hydroxyoctanoate, 3-methylglutarylcarnitine, 3-ureidopropionate, 7-alpha-hydroxy-4-cholesten-3-one (7-Hoca), citrate, fucose, fumarate, gamma-tocopherol, glutamate, glutarate, glycerol, glycochenodeoxycholate, glycocholate, hypoxanthine, maleate, malonate, mannose, orotate, 2,3 pyrdinedicarboxylate, ribose, serine, taurine, taurochenodeoxycholate, taurocholate, palmitoleate, linolenate, xanthine, xylitol, and combinations thereof, is described herein.

In exemplary embodiments, the one or more internal standards for use with the kit may include one or more internal standards selected from the group consisting of 12,13-DiHOME-d4,13C2-Glutarate, 13C415N2-Ureidopropionic acid, 3-Hydroxyoctanoic acid-d12,7a-Hydroxy-4-cholesten-3-one-d7, Citric Acid-2,2,4,4-d4 acid, d4-3-hydroxybutyrate, D-Ribose-13C5, Fucose-13C6, Fumaric acid-13C4, Gamma-Tocopherol-d4, Glycerol 13C3, Glycochenodeoxycholic-d4 acid, Glycocholic-d4 acid, Hypoxanthine-13C5,15N4, L-Glutamic acid-d5, L-Serine (2,3,3-d3), Maleic acid 2,3-d2, Malonic Acid-d4, Mannose 13C6, Palmitoleic Acid-d14, Quinolinic acid 13C315N, Taurine-1,1,2,2-d4, Taurochenodeoxycholate-d4, Taurocholate-d4, Xylitol-d7, d4-linolenic acid, xanthine-13C15N2, orotate-13C15N2, 3-methyl-glutaroylN-(methyl-d3)-carnitine, and combinations thereof.

In one embodiment, a kit for assaying one or more of the liver panel analytes selected from the group consisting of 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, Linolenic acid, and combinations thereof, is described herein. The internal standards for use with the kit may be selected from the group consisting of 12,13-DiHOME-d4, 3-Hydroxyoctanoic acid-d12, Citric Acid-2,2,4,4-d4 acid, Fucose-13C6, Glycerol 13C3, Glycochenodeoxycholic-d4 acid, Glycocholic-d4 acid, Malonic Acid-d4, Palmitoleic Acid-d14, L-Serine (2,3,3-d3), Taurine-1,1,2,2-d4, Taurochenodeoxycholate-d4, Taurocholate-d4, Xanthine-13C15N2, Xylitol-d7, and d4-Linolenic acid.

In another embodiment, a kit for assaying one or more of the liver panel analytes selected from the group consisting of 12,13-DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, Taurocholate, and combinations thereof, is described herein. The internal standards for use with the kit may be selected from the group consisting of 12,13-DiHOME-d4, 3-methyl-glutaroylN-(methyl-d3)-carnitine, 7a Hydroxy-4-cholesten-3-one-d7, Gamma-Tocopherol-d4, Glutamic acid-d5, Glycochenodeoxycholic-d4 acid, Glycocholic-d4 acid, Hypoxanthine-13C5,15N4, L-L-Serine (2,3,3-d3), and Taurocholate-d4.

In another embodiment, a kit for assaying one or more of the liver panel analytes selected from the group consisting of 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, Xylitol, and combinations thereof, is described herein. The internal standards for use with the kit may be selected from the group consisting of Quinolinic acid 13C315N, d4-3-hydroxybutyrate, Fucose-13C6, Fumaric acid-13C4, L-Glutamic acid-d5, 13C2-Glutarate, Glycerol 13C3, Hypoxanthine-13C5, 15N4, Maleic acid 2,3-d2, Malonic Acid-d4, Mannose 13C6, orotate-13C15N2, D-Ribose-13C5, L-Serine (2,3,3-d3), Taurine-1,1,2,2-d4, 13C415N2-Ureidopropionic acid, xanthine-13C15N2, and Xylitol-d7.

EXAMPLES

I. Sample Preparation

A. Reagents and Instruments

Mass spectrometric grade (98%) formic acid and ammonium formate (>98%) were obtained from Sigma-Aldrich; HPLC grade methanol and acetonitrile were obtained from JT Baker; and Hydrochloric acid, 6N(Certified) was obtained from Fisher Scientific. A Multi-Tube Vortexer from VWR Scientific was used for mixing. Centrifugation of plates was carried out in a Sorvall ST 40R centrifuge from Thermo Scientific with a 3617 bucket rotor. Internal standards were obtained from commercial sources.

B. Sample Preparation

Samples were thawed on ice and vortexed. To extract the analytes from the study samples and QC samples, 450 µL of methanol, and 30 µL of a working internal standard (WIS) solution containing the appropriate internal standard(s) was added to sample. The WIS solution may be comprised of one or more internal standards and may comprise one or more internal standards for each of the analytes described herein. The sample blanks were extracted by adding 450 µL of methanol and 30 µL of WIS solvent without internal standards. The determination of WIS concentration may be based on, for example, the concentrations of the analyte in the calibration range. For example, the concentration of the WIS an analyte may be about the concentration of calibration standards C and D for the analyte.

The calibration ranges of the analytes were determined. The calibration ranges for each analyte are listed in Table 1. For each analyte, the LLOQ represents the low end of the calibration range, and the high end of the calibration range is represented by the ULOQ. One of ordinary skill in the art would understand how to determine the calibration range for each analyte without undue experimentation. In one example, eight calibrators (standards A-H) may be used to cover the calibration ranges. Calibration spiking solutions may be prepared at 20-fold of the corresponding calibration concentrations.

TABLE 1

Calibration Ranges for Analytes

| Analyte | Calibration Range (ng/mL) |
| --- | --- |
| glutarate | 10-1000 |
| Orotate | 2.5-250 |
| xanthine | 10-1000 |
| Fucose | 1000-100,000 |
| fumaric acid | 10-1000 |
| glycerol | 2500-250,000 |
| hypoxanthine | 50-5000 |
| maleic acid | 0.5-50 |
| malonic acid | 2.5-250 |
| mannose | 500-50000 |
| 2,3-pyridinedicarboxylic acid (quinolinic acid) | 10-1000 |
| Ribose | 500-50000 |
| Serine | 1000-100,000 |
| Taurine | 500-50,000 |
| Xylitol | 50-5000 |
| 3-HB (BHBA) | 500-50000 |
| 3-ureidopropionic acid | 5-500 |
| 3-Methylglutaryl L-carnitine | 1-100 |
| gamma-tocopherol | 500-50,000 |

TABLE 1-continued

Calibration Ranges for Analytes

| Analyte | Calibration Range (ng/mL) |
| --- | --- |
| L-Glutamic acid | 5,000-500,000 |
| 12(13)-DiHOME | 2.5-250 |
| 7a-Hydroxy-4-cholesten-3-one | 10-1000 |
| Glycochenodeoxycholate | 50-5000 |
| Glycocholate | 10-1,000 |
| Taurocholate | 5-500 |
| 3-Hydroxyoctanoic acid | 10-1000 |
| Citric Acid | 2500-250,000 |
| taurochenodeoxycholate | 10-1000 |
| Palmitoleic acid | 1000-100,000 |
| gamma-Linolenic acid | 1,000-100,000 |

QC levels may be determined based on LLOQ and ULOQ. Low, mid, and high level QC samples may be prepared from human serum pools of appropriate analyte concentrations with fortification of analytes as necessary. LLOQ samples may be prepared in a fatty-acid free BSA solution (7.5% in PBS) at the same concentrations as, for example, standard A for all analytes. QC samples may be stored at −80° C.

For sample analysis, 25 µL of the extracted sample was transferred to the appropriate wells of the plate. The plate was sealed and mixed on a plate shaker at high speed for approximately 2 minutes. The plate was centrifuged at 4° C. for 10 minutes at 4,000 rpm; and an aliquot of 150 µL of the supernatant was transferred to a new plate for LC-MS/MS analysis. To assess sample recovery, medium QC samples may be spiked with a concentration equivalent to calibration standard E. Stock solutions, calibration spiking solutions, and internal standard solutions were stored at 4° C.

Example 1: Chromatographic Purification and Separation of Analytes from Samples

Chromatographic methods were developed using UHPLC to analyze one or more and up to eighteen analytes from a single injection. For each chromatographic method a single fixed aliquot of 1.0 µL of the final extraction solution was injected onto the UPLC column for each sample analyzed. An Agilent 1290 Infinity UHPLC system equipped with a binary solvent pump unit, a refrigerated autosampler, and a column heater was used for liquid chromatography with a reversed phase column (Waters ACQUITY BEH C18, 1.7 µm, 2.1×100 mm) for Chromatography Methods 1 & 2 and with a HILIC column (Waters ACQUITY UPLC® BEH Amide, 1.7 µm, 2.1×150 mm) for Chromatography Method 3. Each chromatography method is further exemplified below.

A. Chromatography Method 1

In one example, a liquid chromatography method was developed for the purification and separation in the same injection of one or more, two or more, and up to all sixteen analytes selected from the group consisting of 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, and Linolenic acid and combinations thereof.

Mobile phase A was ammonium bicarbonate in water, and mobile phase B was ammonium bicarbonate in methanol and water. Linear gradient elution was carried out with an initial condition of 0.5% mobile phase B and 350 µL/min flow rate. The total run time was 7.5 minutes.

Chromatography Method 1 separated a plurality of up to sixteen analytes with good peak shapes. Approximate retention times (in minutes) were 5.27, 3.59, 0.62, 0.857, 0.807, 5.37, 5.28, 0.783, 5.63, 0.731, 0.732, 5.36, 5.28, 0.832, 0.768, and 5.53 for 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, and Linolenic acid, respectively.

B. Chromatography Method 2

In another example, a liquid chromatography method was developed for the purification and separation in the same injection of one or more, two or more, and up to all ten analytes selected from the group consisting of 12,13-DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, and Taurocholate and combinations thereof.

Mobile phase A was PFPA, formic acid and water and mobile phase B was PFPA, formic acid, and methanol. Linear gradient elution was carried out with an initial condition of 5% mobile phase B and 450 µL/min flow rate. The total run time was 9.0 min.

Chromatography Method 2 separated a plurality of up to ten analytes with good peak shapes. Approximate retention times (in minutes) were 5.17, 2.85, 6.16, 3.33, 1.07, 5.16, 4.87, 0.998, 0.878, and 4.51 for 12,13-DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, and Taurocholate, respectively.

C. Chromatography Method 3

In another example, a liquid chromatography method was developed for the purification and separation in the same injection of one or more, two or more, and up to all eighteen analytes selected from the group consisting of 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, and Xylitol and combinations thereof.

Mobile phase A was ammonium formate, acetonitrile, methanol, and water, and mobile phase B was ammonium formate and acetonitrile. Linear gradient elution was carried out with an initial condition of 5% mobile phase B and 500 µL/min flow rate. The total run time was 7.5 min.

Chromatography Method 3 separated a plurality of up to eighteen analytes with good peak shapes. Approximate retention times (in minutes) were 3.49, 1.58, 1.75, 3.27, 3.22, 3.41, 1.29, 1.59, 2.62, 3.72, 2.39, 1.74, 1.56, 3.25, 2.04, 2.44, 2.14, and 2.00, for 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, and Xylitol, respectively.

Example 2: MS/MS Measurement of Analytes

Mass spectrometry was performed on the sample extracts as described in the methods below using an AB Sciex QTrap 5500 mass spectrometer with Turbo V source (ESI). Raw data were acquired from the instrument and processed using Analyst 1.6.2 software (AB Sciex). For quantitation, peak area ratios of analyte to internal standard were fitted against the concentrations of the calibration standards by weighted ($1/x^2$) linear least squares regression. The resulting slope and intercept of the calibration curve were used to calculate the unknown concentrations in experimental samples.

A. MS/MS Method 1

A method was developed to detect in a single injection the levels of one or more, two or more, and up to all sixteen analytes selected from the group consisting of 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, and Linolenic acid and combinations thereof.

The same MS/MS method was used to detect, in a separate single injection, the levels of one or more, two or more, and up to all eighteen analytes selected from the group consisting of 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, and Xylitol and combinations thereof.

The eluent from the chromatography column described in Example 1, Chromatography Method 1, was directly and automatically introduced into the electrospray source of a mass spectrometer. In another example, the eluent from the chromatography column described in Example 1, Chromatography Method 3, was directly and automatically introduced into the electrospray source of a mass spectrometer. Methanol or isopropanol was used for needle wash. The instrument was operated in negative multiple reaction monitoring (MRM) mode. Ionspray voltage was set at −4.5 kV, source temperature at 500° C., curtain gas (e.g., nitrogen) at 30 psi, and nebulizer and desolvation gas (e.g., nitrogen) flow rates at 70 psi, collisionally activated dissociation (CAD) gas (e.g., nitrogen) at medium.

Raw data were acquired from the instrument and processed using Analyst 1.6.2 software (AB Sciex). For quantitation, peak area ratios of analyte to internal standard were fitted against the concentrations of the calibration standards by weighted ($1/x^2$) linear least squares regression. The resulting slope and intercept of the calibration curve were used to calculate the unknown concentrations in experimental samples. Exemplary ions that were generated for the quantitation of 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, and Linolenic acid are listed in Table 2. Exemplary ions that were generated for the quantitation of 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, and Xylitol are listed in Table 3. The parent ions are listed under the column headed "Parent ion (m/z)", and the daughter ions used for quantitation in this example are listed in the column labeled "Daughter ion for quantitation (m/z)". The choice of daughter ion for quantitation in this example was optimized for sensitivity across the analytical measurement range; however, additional daughter ions may be selected to replace or augment the daughter ions used for quantitation in the examples.

TABLE 2

Parent and Daughter Ion Mass-to-Charge Ratios (m/z) of Analytes from Chromatography Method 1 / MS Method 1

| Analyte | Parent Ion (m/z) | Daughter Ion for quantitation (m/z) | Additional Daughter Ions (m/z, ±0.5) |
|---|---|---|---|
| 3-Hydroxyoctanoic acid | 159.02 ± 0.5 | 59 ± 0.5 | 61.1, 71.2, 77.0, 79.2, 79.9, 95.0, 97.0, 99.1, 110.9, 113.0, 115.0, 159.0 |
| 3-Hydroxyoctanoic acid-d12 | 171.04 ± 0.5 | 59 ± 0.5 | 60.0, 61.0, 75.0, 77.0, 90.8, 95.0, 109.1, 127.0, 138.8, 171.2 |
| 12,13-DiHOME | 313.1 ± 0.5 | 183.1 ± 0.5 | 58.0, 59.0, 94.9, 97.1, 99.0, 101.1, 125.2, 127.1, 129.0, 181.0, 184.9, 195.1, 277.2, 295.1, 313.1 |
| 12,13-DiHOME-d4 | 317.3 ± 0.5 | 185.0 ± 0.5 | 58.9, 60.0, 61.2, 100.1, 101.1, 128.1, 130.0, 131.0, 132.0, 184.0, 186.1, 197.0, 198.0, 199.1, 279.2, 280.2, 281.1, 299.2, 317.3 |
| Glycochenodeoxycholate | 448.22 ± 0.5 | 386.3 ± 0.5 | 61.0, 72.0, 74.0, 83.9, 188.8, 289.9, 292.3, 330.1, 368.2, 384.2, 402.1, 404.2, 448.2 |
| Glycochenodeoxycholic-d4 acid | 452.19 ± 0.5 | 390.2 ± 0.5 | 71.9, 74.0, 84.0, 290.2, 330.1, 331.2, 387.3, 389.1, 406.2, 408.2, 452.4 |
| Glycocholate | 464.16 ± 0.5 | 74.0 ± 0.5 | 69.0, 72.1, 95.0, 261.9, 264.2, 380.3, 382.2, 384.1, 398.3, 400.2, 402.2, 418.2, 420.2, 464.2 |
| Glycocholic-2,2,4,4-d4 acid | 468.18 ± 0.5 | 73.9 ± 0.5 | 71.0, 97.0, 98.0, 262.1, 263.2, 264.2, 402.2, 403.2, 404.2, 406.2, 450.3, 468.2 |
| Taurochenodeoxycholate | 498.14 ± 0.5 | 79.9 ± 0.5 | 81.0, 107.0, 124.2, 172.0, 189.0, 372.3, 373.1, 384.3, 386.3, 414.2, 416.2, 480.4, 498.4 |
| Taurochenodeoxycholate-d4 | 502.32 ± 0.5 | 79.9 ± 0.5 | 81.0, 93.9, 107.0, 124.0, 188.8, 294.6, 334.8, 484.3, 502.4 |
| Taurocholate | 514.16 ± 0.5 | 79.9 ± 0.5 | 81.0, 107.0, 124.0, 434.2, 452.2, 470.2, 496.1, 514.2 |
| Taurocholate-2,2,4,4-d4 | 518.19 ± 0.5 | 79.9 ± 0.5 | 81.0, 93.9, 106.8, 124.0, 188.9, 357.1, 500.4, 518.2 |
| Palmitoleic Acid | 255.14 ± 0.5 | 237.2 ± 0.5 | 54.1, 79.8, 81.1, 178.8, 183.8, 195.6, 218.8, 235.2, 255.2 |
| Palmitoleic Acid-d14 | 267.19 ± 0.5 | 222.9 ± 0.5 | 60.0, 82.8, 97.1, 99.1, 116.8, 121.1, 122.7, 139.0, 182.9, 204.9, 222.9, 249.2, 267.2 |
| y-Linolenic acid | 277.12 ± 0.5 | 205.1 ± 0.5 | 59.0, 60.8, 81.0, 83.0, 93.1, 94.8, 97.0, 98.9, 177.2, 179.0, 203.1, 230.9, 233.0, 233.0, 257.2, 259.0, 275.2, 277.2 |
| d4-linolenic acid | 281.1 ± 0.5 | 209.1 ± 0.5 | 58.9, 71.0, 79.9, 183.1, 209.0, 211.1, 251.0, 265.2, 267.0, 281.1 |
| Citric Acid | 190.92 ± 0.5 | 130.9 ± 0.5 | 57.0, 58.9, 67.0, 85.2, 87.0, 110.8, 129.0, 146.8, 154.6, 173.0, 191.0 |
| Citric Acid-2,2,4,4-d4 acid | 194.95 ± 0.5 | 132 ± 0.5 | 58.8, 60.2, 61.2, 69.2, 70.0, 86.9, 88.0, 89.0, 90.1, 112.2, 112.8, 114.0, 131.0, 133.2, 150.8, 175.8, 177.0, 195.0 |
| Fucose | 162.97 ± 0.5 | 59 ± 0.5 | 55.1, 61.0, 71.0, 73.0, 83.0, 85.2, 89.0, 98.9, 100.8, 103.0, 119.0, 127.2, 145.0, 163.0 |
| (UL-13C6) Fucose | 168.99 ± 0.5 | 60.9 ± 0.5 | 59.0, 74.0, 76.2, 89.2, 92.0, 105.0, 107.0, 123.0, 133.2, 150.8, 169.0 |
| Glycerol | 90.92 ± 0.5 | 59.1 ± 0.5 | 57.0, 59.9, 61.0, 70.9, 75.0, 91.0 |
| Glycerol 13C3 | 94.86 ± 0.5 | 60 ± 0.5 | 58.9, 76.0, 77.0, 95.0 |

TABLE 2-continued

Parent and Daughter Ion Mass-to-Charge Ratios (m/z) of Analytes from
Chromatography Method 1 / MS Method 1

| Analyte | Parent Ion (m/z) | Daughter Ion for quantitation (m/z) | Additional Daughter Ions (m/z, ±0.5) |
|---|---|---|---|
| Malonic Acid | 102.9 ± 0.5 | 73 ± 0.5 | 59.0, 71.0, 102.9 |
| Malonic Acid-d4 | 105.89 ± 0.5 | 73 ± 0.5 | 61.0, 76.0, 105.9 |
| Serine | 103.92 ± 0.5 | 74 ± 0.5 | 56.0, 58.0, 60.0, 72.0, 104.0 |
| Serine (2,3,3-d3) | 106.89 ± 0.5 | 74.9 ± 0.5 | 59.0, 60.0, 61.0, 63.0, 77.0, 107.0 |
| Taurine | 123.91 ± 0.5 | 79.9 ± 0.5 | 61.0, 61.8, 64.0, 65.0, 81.0, 92.0, 95.0, 107.0, 123.9 |
| Taurine-1,1,2,2-d4 | 127.92 ± 0.5 | 80 ± 0.5 | 60.0, 64.0, 66.0, 77.0, 77.9, 80.8, 82.0, 94.8, 97.0, 109.8, 128.0 |
| Xanthine | 150.95 ± 0.5 | 108 ± 0.5 | 53.0, 66.2, 78.8, 79.8, 132.8, 136.2, 160.0 |
| Xanthine-13C,15N2 | 154.0 | 110.0 | 65.8, 76.9, 80.9, 108.8, 120.9, 136.1, 154.0 |
| Xylitol | 150.98 ± 0.5 | 89 ± 0.5 | 55.0, 57.0, 59.0, 59.8, 59.0, 61.0, 69.2, 71.0, 73.0, 75.0, 77.0, 83.0, 84.8, 91.0, 101.0, 103.0, 107.0, 108.2, 113.2, 118.8, 121.0, 130.8, 133.2, 136.0, 149.2, 151.0 |
| Xylitol-d7 | 158.02 ± 0.5 | 92.1 ± 0.5 | 57.0, 58.0, 60.1, 61.2, 62.0, 71.9, 72.8, 74.2, 76.0, 77.2, 85.8, 88.8, 90.0, 90.8, 93.0, 94.2, 95.2, 95.8, 102.2, 104.0, 105.0, 108.4, 118.0, 123.2, 136.0, 136.8, 140.0, 155.0, 158.2 |

TABLE 3

Parent and Daughter Ion Mass-to-Charge Ratios (m/z) of Analytes from
Chromatography Method 3/ MS Method 1

| Analyte | Parent Ion (m/z) | Daughter Ion for quantitation (m/z) | Additional Daughter Ions (m/z, ±0.5) |
|---|---|---|---|
| Glutarate | 131.000 ± 0.5 | 87.000 ± 0.5 | 59.2, 69.2, 70.8, 84.0, 85.2, 100.0, 101.0, 113.0, 129.0, 131.0 |
| 13C2-Glutarate | 133.000 ± 0.5 | 88.000 ± 0.5 | 59.2, 60.2, 70.0, 71.2, 72.8, 75.0, 101.0, 103.0, 115.0, 133.0 |
| Orotate | 155.000 ± 0.5 | 110.900 ± 0.5 | 66.0, 67.0, 68.2, 77.0, 91.0, 93.0, 111.0, 137.2, 154.8 |
| orotate-13C,15N2 | 157.960 ± 0.5 | 114.0 ± 0.5 | 66.9, 69.1, 69.9, 76.9, 77.9, 95.0, 96.0, 158.0 |
| Xanthine | 150.950 ± 0.5 | 107.950 ± 0.5 | 53.0, 66.2, 78.8, 79.8, 132.8, 136.2, 160.0 |
| Xanthine-13C,15N2 | 153.970 ± 0.5 | 110.000 ± 0.5 | 65.8, 76.9, 80.9, 108.8, 120.9, 136.1, 154.0 |
| 3-Ureidopropionic acid | 130.951 ± 0.5 | 87.965 ± 0.5 | 58.8, 60.2, 71.0, 85.0, 101.0, 114.0, 131.0 |
| 13C4,15N2-Ureidopropionic acid | 136.950 ± 0.5 | 91.965 ± 0.5 | 76.0 |
| Fucose | 162.965 ± 0.5 | 59.000 ± 0.5 | 55.1, 61.0, 71.0, 73.0, 83.0, 85.2, 89.0, 98.9, 100.8, 103.0, 119.0, 127.2, 145.0, 163.0 |
| Fucose_13C6 | 168.985 ± 0.5 | 61.000 ± 0.5 | 59.0, 74.0, 76.2, 89.2, 92.0, 105.0, 107.0, 123.0, 133.2, 150.8, 169.0 |
| Fumaric acid | 114.894 ± 0.5 | 70.985 ± 0.5 | 59.0, 79.2, 85.2, 96.8, 98.8, 114.8 |
| Fumaric acid_13C4 | 118.925 ± 0.5 | 74.000 ± 0.5 | 59.0, 61.4, 73.0, 75.0, 80.0, 89.0, 96.0, 101.0, 119.0 |
| Glutamic acid | 145.926 ± 0.5 | 85.000 ±0.5 | 57.0, 59.2, 62.2, 70.8, 72.0, 74.2, 84.2, 85.2, 100.0, 100.8, 102.0, 127.8, 146.0 |

TABLE 3-continued

Parent and Daughter Ion Mass-to-Charge Ratios (m/z) of Analytes from
Chromatography Method 3/ MS Method 1

| Analyte | Parent Ion (m/z) | Daughter Ion for quantitation (m/z) | Additional Daughter Ions (m/z, ±0.5) |
|---|---|---|---|
| Glutamic acid 2,3,3,4,4-d5 | 150.964 ± 0.5 | 90.000 ± 0.5 | 60.0, 60.8, 74.0, 74.8, 76.8, 85.0, 87.0, 88.2, 88.8, 92.2, 105.0, 107.0, 131.0, 132.0, 133.0, 151.0 |
| Glycerol | 90.920 ± 0.5 | 59.100 ± 0.5 | 57.0, 59.9, 61.0, 70.9, 75.0, 91.0 |
| Glycerol 13C3 | 93.900 ± 0.5 | 61.000 ± 0.5 | 58.9, 76.0, 77.0, 95.0 |
| Hypoxanthine | 134.900 ± 0.5 | 65.000 ± 0.5 | 64.0, 66.0, 75.0, 90.8, 92.0, 95.2, 99.6, 105.8, 107.0, 116.8, 132.8, 135.0 |
| Hypoxanthine 13C5,15N4 | 143.900 ± 0.5 | 70.000 ± 0.5 | 68.8, 70.0, 71.0, 73.0, 99.0, 114.0, 115.0, 141.8, 144.0 |
| Maleic acid | 114.900 ± 0.5 | 70.900 ± 0.5 | 59.2, 97.0, 114.8 |
| Maleic acid 2,3-d2 | 116.900 ± 0.5 | 73.000 ± 0.5 | 59.2, 61.0, 75.8, 98.8, 117.0 |
| Malonic acid | 102.900 ± 0.5 | 59.000 ± 0.5 | 59.0, 71.0, 102.9 |
| Malonic acid d4 | 105.900 ± 0.5 | 61.000 ± 0.5 | 61.0, 76.0, 105.9 |
| Mannose | 178.966 ± 0.5 | 119.000 ± 0.5 | 55.2, 57.0, 59.0, 71.0, 73.2, 76.8, 83.2, 84.8, 87.0, 88.8, 95.0, 98.6, 100.8, 107.0, 113.0, 116.6, 125.2, 131.0, 135.2, 143.0, 148.8, 161.0, 179.0 |
| Mannose 13C6 | 184.944 ± 0.5 | 123.000 ± 0.5 | 58.0, 59.2, 61.0, 68.6, 71.2, 74.0, 76.8, 78.8, 87.0, 89.0, 92.2, 97.0, 100.0, 109.0, 117.8, 131.0, 135.8, 140.0, 141.2, 149.0, 152.8, 153.8, 167.0, 185.0 |
| 2,3-pyridinedicarboxylic acid (Quinolinic acid) | 166.000 ± 0.5 | 122.000 ± 0.5 | 51.0, 58.0, 60.2, 75.2, 78.2, 102.2, 134.0, 165.8 |
| Quinolinic acid 13C315N | 170.000 ± 0.5 | 126.000 ± 0.5 | 53.0, 56.2, 60.0, 71.2, 71.8, 82.2, 86.2, 136.0, 138.0, 152.0, 170.0 |
| Ribose | 149.000 ± 0.5 | 89.000 ± 0.5 | 55.0, 57.0, 58.8, 71.0, 84.8, 101.2, 104.8, 112.8, 119.0, 131.0, 146.8, 148.8 |
| Ribose_13C5 | 154.000 ± 0.5 | 92.000 ± 0.5 | 58.0, 58.8, 61.0, 74.0, 77.0, 79.2, 89.0, 92.0, 104.8, 109.4, 117.8, 120.8, 122.8, 135.6, 151.2, 154.0 |
| Serine | 105.000 ± 0.5 | 74.000 ± 0.5 | 56.0, 58.0, 60.0, 72.0, 104.0 |
| Serine 2,3,3-d3 | 106.900 ± 0.5 | 75.000 ± 0.5 | 59.0, 60.0, 61.0, 63.0, 77.0, 107.0 |
| Taurine | 123.900 ± 0.5 | 107.000 ± 0.5 | 61.0, 61.8, 64.0, 65.0, 81.0, 92.0, 95.0, 107.0, 123.9 |
| Taurine 1,1,2,2-d4 | 127.900 ± 0.5 | 110.000 ± 0.5 | 60.0, 64.0, 66.0, 77.9, 80.8, 82.0, 94.8, 97.0, 109.8, 128.0 |
| Xylitol | 151.000 ± 0.5 | 89.000 ± 0.5 | 55.0, 57.0, 59.0, 59.8, 59.0, 61.0, 69.2, 71.0, 73.0, 75.0, 77.0, 83.0, 84.8, 91.0, 101.0, 103.0, 107.0, 108.2, 113.2, 118.8, 121.0, 130.8, 133.2, 136.0, 149.2, 151.0 |
| Xylitol-d7 | 158.000 ± 0.5 | 92.000 ± 0.5 | 57.0, 58.0, 60.1, 61.2, 62.0, 71.9, 72.8, 74.2, 76.0, 77.2, 85.8, 88.8, 90.0, 90.8, 93.0, 94.2, 95.2, 95.8, 102.2, 104.0, 105.0, 108.4, 118.0, 123.2, 136.0, 136.8, 140.0, 155.0, 158.2 |
| 3-HB | 102.900 ± 0.5 | 59.001 ± 0.5 | 57.0, 62.8, 71.2, 73.2, 75.2, 77.0, 82.4, 103.0 |
| d4-3HB | 107.000 ± 0.5 | 59.000 ± 0.5 | 60.0, 61.2, 62.8, 72.8, 76.8, 83.2, 106.8 |

B. MS/MS Method 2

In another example, a method was developed to detect in the same injection the levels of one or more, two or more, and up to all 12,13-DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, and Taurocholate and combinations thereof. The eluent from the chromatography column described in Example 1, Chromatography Method 2, was directly and automatically introduced into the electrospray source of a mass spectrometer. Isopropanol was used for needle wash.

The instruments were operated in positive MRM mode. Ionspray voltage was set at 5.5 kV, source temperature at 500° C., and curtain gas at 30 psi; nebulizer and desolvation gas flow rates were set at 70 psi, and CAD gas at medium.

Exemplary ions that were generated for the quantitation of 12,13-DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, and Taurocholate are shown in Table 4. The parent ions are listed under the column headed "Parent ion (m/z)", and the daughter ions used for quantitation in this example are listed in the column labeled "Daughter ion for quantitation (m/z)". The choice of daughter ion for quantitation in this example was optimized for sensitivity across the analytical measurement range; however, any of the daughter ions may be selected to replace or augment the daughter ions used for quantitation in the examples.

TABLE 4

Parent and Daughter Ion Mass-to-Charge Ratios (m/z) of Analytes from Chromatography Method 2/ MS Method 2

| Analyte | Parent Ion (m/z) | Daughter Ion for quantitation (m/z) | Additional Daughter Ions (m/z, ±0.5) |
|---|---|---|---|
| 3-Methylglutaryl L-carnitine | 290.097 ± 0.5 | 85.000 ± 0.5 | 55.0, 57.1, 58.1, 59.1, 60.0, 83.1, 101.1, 103.2, 129.0, 213.1, 290.1 |
| 3-methyl-glutaroylN-(methyl-d3)-carnitine | 293.0 | 84.9 | 55.1, 57.0, 59.1, 61.0, 63.0, 83.0, 101.1, 103.1, 129.1, 213.1, |
| Gamma-Tocopherol | 417.303 ± 0.5 | 343.700 ± 0.5 | 59.0, 65.1, 66.9, 67.9, 69.0, 71.0, 77.0, 78.0, 79.0, 79.9, 80.9, 93.1, 94.1, 95.0, 96.0, 105.0, 106.0, 106.9, 107.9, 109.1, 121.1, 122.0, 123.1, 124.1, 150.0, 151.1, 152.1, 153.1, 417.3 |
| Gamma-Tocopherol-d4 | 421.345 ± 0.5 | 99.000 ± 0.5 | 66.9, 68.0, 69.0, 70.0, 71.0, 77.0, 78.0, 78.9, 80.0, 81.1, 82.0, 97.1, 97.9, 99.0, 100.0, 109.0, 109.9, 111.0, 112.0, 113.1, 125.1, 126.1, 127.1, 128.1, 153.2, 154.1, 155.2, 156.2, 157.0, 421.3 |
| L-Glutamic acid | 147.978 ± 0.5 | 102.100 ± 0.5 | 54.9, 56.0, 57.0, 83.9, 85.0, 130.1, 131.0, 148.0 |
| L-Glutamic acid-d5 | 153.023 ± 0.5 | 89.000 ± 0.5 | 58.9, 60.0, 61.0, 76.9, 79.1, 86.9, 88.0, 89.0, 89.9, 91.0, 95.0, 97.0, 106.2, 107.2, 109.1, 134.2, 135.1, 136.1, 153.0 |
| Hypoxanthine | 136.973 ± 0.5 | 82.000 ± 0.5 | 53.1, 55.1, 65.0, 66.0, 67.0, 77.0, 79.1, 81.0, 82.9, 91.0, 91.9, 93.0, 94.0, 95.2, 109.2, 110.1, 119.1, 120.0, 137.0 |
| Hypoxanthine-13C5,15N4 | 145.995 ± 0.5 | 88.000 ± 0.5 | 56.9, 59.0, 70.0, 72.1, 83.0, 99.1, 101.0, 117.1, 128.0, 146.0 |
| L-Serine | 105.980 ± 0.5 | 60.000 ± 0.5 | 50.1, 50.9, 56.0, 57.9, 65.0, 59.9, 74.0, 78.0, 88.0, 88.9, 106.0 |
| L-Serine-d3 | 108.968 ± 0.5 | 63.000 ± 0.5 | 51.0, 53.1, 55.1, 65.1, 65.9, 67.0, 73.0, 77.1, 79.0, 80.1, 81.0, 91.0, 109.0 |
| 12(13)-DiHOME | 315.220 ± 0.5 | 279.200 ± 0.5 | 52.9, 55.0, 57.0, 65.1, 66.9, 69.1, 77.0, 79.0, 81.0, 83.0, 91.0, 93.0, 94.9, 96.9, 105.1, 106.9, 280.9, 297.2, 315.2 |
| 12(13)-DiHOME-d4 | 319.246 ± 0.5 | 283.200 ± 0.5 | 53.0, 54.0, 55.1, 56.1, 57.0, 66.1, 67.0, 68.0, 69.1, 70.0, 71.0, 72.0, 79.1, 80.1, 81.0, 82.0, 83.0, 84.1, 85.1, 281.1, 282.2, 300.1, 301.3, 319.2 |
| 7a-Hydroxy-4-cholesten-3-one | 401.217 ± 0.5 | 383.300 ± 0.5 | 53.1, 55.1, 57.1, 75.0, 77.0, 79.0, 81.0, 82.9, 90.9, 92.9, 95.0, 97.1, 116.0, 359.8, 383.3, 401.2 |
| 7a-Hydroxy-4-cholesten-3-one-d7 | 408.317 ± 0.5 | 390.300 ± 0.5 | 53.1, 55.0, 56.0, 57.0, 65.1, 67.0, 69.1, 75.0, 77.0, 79.0, 81.0, 83.1, 91.1, 93.0, 95.1, 97.1, 98.1, 119.2, 121.1, 123.1, 147.1, 149.0, 408.3 |
| Glycochenodeoxycholate | 450.286 ± 0.5 | 414.300 ± 0.5 | 53.0, 55.0, 57.1, 65.0, 67.0, 69.0, 75.1, 76.1, 77.1, 79.0, 81.1, 83.0, 90.9, 93.0, 103.1, 105.0, 107.0, 339.2, 414.3, 450.3 |
| Glycochenodeoxycholic-d4 acid | 454.321 ± 0.5 | 418.300 ± 0.5 | 65.2, 67.1, 68.1, 69.2, 77.0, 78.1, 79.0, 80.1, 81.0, 81.9, 83.1, 90.9, 92.0, 92.8, 94.0, 95.2, 102.9, 105.1, 105.9, 107.0, 341.2, 342.2, 343.3, 417.3, 436.3, 454.3 |
| Glycocholate | 448.251 ± 0.5 | 412.200 ± 0.5 | 53.0, 55.0, 56.0, 57.0, 65.1, 67.1, 69.1, 77.0, 78.0, 79.0, 81.1, 88.9, 91.0, 92.9, 103.0, 105.0, 106.9, 319.2, 337.2, 412.2, 430.3, 448.2 |
| Glycocholic-d4 acid | 470.311 ± 0.5 | 341.300 ± 0.5 | 53.0, 55.2, 55.9, 57.0, 77.0, 78.0, 79.1, 79.9, 81.0, 90.9, 92.0, 93.2, 103.0, 105.0, 105.9, 107.0, 209.1, 210.1, 211.1, 322.1, 323.3, 340.2, 341.3, 416.3, 434.3, 470.3 |

TABLE 4-continued

Parent and Daughter Ion Mass-to-Charge Ratios (m/z) of Analytes from Chromatography Method 2/ MS Method 2

| Analyte | Parent Ion (m/z) | Daughter Ion for quantitation (m/z) | Additional Daughter Ions (m/z, ±0.5) |
|---|---|---|---|
| Taurocholate | 516.214 ± 0.5 | 462.200 ± 0.5 | 55.0, 67.0, 77.1, 79.0, 81.0, 91.0, 92.9, 105.0, 126.0, 319.1, 337.2, 516.2 |
| Taurocholate-d4 | 520.269 ± 0.5 | 466.300 ± 0.5 | 55.0, 91.0, 92.0, 93.1, 126.1, 127.1, 208.0, 209.1, 210.2, 322.2, 323.2, 340.2, 341.2, 465.2, 484.2, 502.3, 504.0, 520.3 |

Example 3: Quantitative Measurement of Analytes in Experimental Samples

Six serum samples were prepared as indicated in I. B. Sample Preparation section above. Analytes were measured in the experimental samples using the LC and MS methods described in Examples 1 and 2. The methods were used to determine the absolute amount (concentration) of the analytes 12,13-DiHOME, 3-hydroxybutyrate (BHBA, 3-HB), 3-hydroxyoctanoate (3-hydroxyoctanoic acid), 3-methylglutarylcarnitine, 3-ureidopropionate (3-ureidopropionic acid), 7-alpha-hydroxy-4-cholesten-3-one (7-Hoca), citrate (citric acid), fucose, fumarate (fumaric acid), gamma-tocopherol, glutamate (glutamic acid), glutarate (glutaric acid), glycerol, glycochenodeoxycholate (glycochenodeoxycholic acid), glycocholate (glycocholic acid), hypoxanthine, maleate (maleic acid), malonate (malonic acid), mannose, orotate (orotic acid), 2,3-pyrdinedicarboxylate, ribose, serine, taurine, taurochenodeoxycholate (taurochenodeoxycholic acid), taurocholate (taurocholic acid), palmitoleate (palmitoleic acid), linolenate (linolenic acid), xanthine, xylitol in serum samples.

Using Chromatography Method 1 and MS Method 1, the analytes 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, and Linolenic acid were measured in a single injection with a run time of 7.5 minutes.

Using Chromatography Method 2 and MS Method 2, the analytes 12,13-DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, and Taurocholate were measured in a single injection with a run time of 9.0 minutes.

Using Chromatography Method 3 and MS Method 1, the analytes 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, and Xylitol were measured in a single injection with a run time of 7.5 minutes.

The measured amounts of the analytes in the six serum samples were determined using the described methods. The measured analyte level for all six serum samples were averaged, and the concentrations (ng/mL) of the analytes are presented in Table 5.

TABLE 5

Results from Representative Serum Samples

| Analyte | Chromatography/Mass Spectrometry Method: Concentration (ng/mL) | | |
|---|---|---|---|
| | LC1 + MS1 | LC2 + MS 2 | LC3 + MS1 |
| glutarate | | | 51.9 |
| Orotate | | | 24.5 |
| xanthine | 96.9 | | 261.8 |
| Fucose | 82007.0 | | 4852.2 |
| fumaric acid | | | 96.5 |
| glycerol | 20000 | | 42500.0 |
| hypoxanthine | | 1202.2 | 1079.7 |
| maleic acid | | | 2.9 |
| malonic acid | | | 16.5 |
| mannose | | | 11641.7 |
| 2,3-pyridinedicarboxylic acid (quinolinic acid) | | | 81.0 |
| Ribose | | | 5860.0 |
| Serine | 26083.0 | 20233.3 | 20066.7 |
| Taurine | 7963.3 | | 5855.0 |
| Xylitol | 2493.0 | | 678.2 |
| 3-HB (BHBA) | | | 3123.3 |
| 3-ureidopropionic acid | | | 19.6 |
| 3-Methylglutaryl L-carnitine | | 7.9 | |
| gamma-tocopherol | | 6175.0 | |
| L-Glutamic acid | | 83816.7 | |
| 12(13)-DiHOME | 7.8 | 10.8 | |
| Glycochenodeoxycholate | 879.7 | 771.3 | |
| Glycocholate | 107.1 | 106.9 | |
| Taurocholate | 106.8 | 104.9 | |
| 3-Hydroxyoctanoic acid | 31.9 | | |
| Citric Acid | 34667.0 | | |
| taurochenodeoxycholate | 113.0 | | |
| Palmitoleic acid | 41450.0 | | |
| gamma-Linolenic acid | 10660.0 | | |

What is claimed:

1. A method for determining in a sample, by mass spectrometry, the amount of three or more analytes selected from the group consisting of 12,13-DiHOME, 3-hydroxybutyrate (BHBA), 3-hydroxyoctanoate, 3-methylglutarylcarnitine, 3-ureidopropionate, 7-alpha-hydroxy-4-cholesten-3-one (7-Hoca), citrate, fucose, fumarate, gamma-tocopherol, glutamate, glutarate, glycerol, glycochenodeoxycholate, glycocholate, hypoxanthine, maleate, malonate, mannose, orotate, 2,3-pyrdinedicarboxylate, ribose, serine, taurine, taurochenodeoxycholate, taurocholate, palmitoleate, linolenate, xanthine, xylitol, and combinations thereof, the method comprising:
   a) subjecting the sample to an ionization source under conditions suitable to produce one or more ions detectable by mass spectrometry from each of the three or more of the analytes, wherein the analytes are not derivatized prior to ionization;
   b) measuring, by mass spectrometry, the amount of the one or more ions from each of the three or more analytes; and
   c) using the measured amount of the one or more ions to determine the amount of each of the three or more analytes in the sample.

2. The method of claim 1, wherein the three or more analytes are selected from the group consisting of 12,13-DiHOME, 3-hydroxyoctanoic acid, Citric Acid, Fucose, Glycerol, Glycochenodeoxycholate, Glycocholate, Malonic Acid, Palmitoleic Acid, Serine, Taurine, Taurochenodeoxycholate, Taurocholate, Xanthine, Xylitol, and Linolenic acid and wherein the amount(s) of the three or more analytes are determined in a single injection.

3. The method of claim 1, wherein the three or more analytes are selected from the group consisting of 12,13-

DiHOME, 3-Methylglutaryl L-carnitine, 7-alpha-hydroxy-4-cholesten-3-one (7-Hoca), Gamma-Tocopherol, Glutamic acid, Glycochenodeoxycholate, Glycocholate, Hypoxanthine, Serine, and Taurocholate and wherein the amount(s) of the three or more analytes are determined in a single injection.

4. The method of claim 3, wherein the ionization source is operated in positive ionization mode.

5. The method of claim 1, wherein the three or more analytes are selected from the group consisting of 2,3-pyridinedicarboxylic acid, 3-hydroxybutyrate, Fucose, Fumaric acid, Glutamic acid, Glutarate, Glycerol, Hypoxanthine, Maleic acid, Malonic Acid, Mannose, Orotate, Ribose, Serine, Taurine, 3-ureidopropionic acid, Xanthine, and Xylitol and wherein the amount(s) of the three or more analytes are determined in a single injection.

6. The method of claim 1, wherein the ionization source is operated in negative ionization mode.

7. The method of claim 1, wherein the one or more ions used to determine the amount of each of the three or more analytes are one or more ions selected from the ions in Tables 2, 3, and 4.

8. The method of claim 1, wherein the sample has been purified by liquid chromatography prior to being subjected to an ionization source.

9. The method of claim 8, wherein said liquid chromatography is selected from the group consisting of high performance liquid chromatography, ultra high performance liquid chromatography, and turbulent flow liquid chromatography.

10. The method of any of claim 1, wherein an internal standard is used to determine the amount of the one or more analytes in the sample.

11. The method of claim 1, wherein the mass spectrometry is tandem mass spectrometry.

12. The method of claim 1, further comprising analyzing the sample using other methods useful in the clinical determination of liver function.

13. The method of claim 12, wherein the other methods are selected from the group consisting of total cholesterol, total triglycerides, albumin, albumin/globulin ratio, total protein, direct bilirubin, total bilirubin, alanine aminotransferase (ALT), aspartate aminotransferase (AST), alkaline phosphatase (ALP), gamma-glutamyl transferase (GGT), and serum cholinesterase (ChE).

* * * * *